United States Patent [19]
Greff

[11] Patent Number: 6,051,607
[45] Date of Patent: Apr. 18, 2000

[54] VASCULAR EMBOLIZING COMPOSITIONS COMPRISING ETHYL LACTATE AND METHODS FOR THEIR USE

[75] Inventor: Richard J. Greff, St. Pete Beach, Fla.

[73] Assignee: Micro Therapeutics, Inc., Irvine, Calif.

[21] Appl. No.: 09/109,041

[22] Filed: Jul. 2, 1998

[51] Int. Cl.$^7$ .................... A61K 31/215; A61K 31/72; A61K 31/74; A61K 49/04; A61M 25/00

[52] U.S. Cl. .................... 514/546; 424/9.4; 424/9.411; 424/9.42; 424/78.08; 514/57; 514/529; 604/96; 604/508; 604/523

[58] Field of Search .................... 424/9.4, 9.41, 424/9.411, 9.42, 9.43, 78.08; 514/57, 506, 529, 546, 834, 930; 604/264, 52, 53, 56, 49, 96, 523, 508, 509, 507; 206/569, 570, 571

[56] References Cited

U.S. PATENT DOCUMENTS

| | | | |
|---|---|---|---|
| 3,527,224 | 9/1970 | Rabinowitz et al. | 606/214 |
| 3,591,676 | 7/1971 | Hawkins et al. | 424/78.06 |
| 4,468,224 | 8/1984 | Enzmann et al. | 604/247 |
| 5,324,519 | 6/1994 | Dunn et al. | 424/426 |
| 5,580,568 | 12/1996 | Greff et al. | 424/423 |
| 5,637,086 | 6/1997 | Ferguson et al. | 604/508 |
| 5,667,767 | 9/1997 | Greff et al. | 429/9.411 |
| 5,695,480 | 12/1997 | Evans et al. | 604/264 |
| 5,702,361 | 12/1997 | Evans et al. | 604/508 |

FOREIGN PATENT DOCUMENTS

| | | |
|---|---|---|
| 92/11845 | 7/1992 | WIPO. |
| 93/10163 | 5/1993 | WIPO. |

OTHER PUBLICATIONS

JP 53039979 A2, (ISHII et al.), Cellulose acetate semipermeable membranes (Apr. 1978), STN/CAS,CAPLUS, Abstract.

JP 58058114 A2, (TSUGAYA et al.), Ultrafiltration membrane for artificial kidney (Apr. 1983), STN/CAS, CAPLUS, Abstract.

Brothers, M.F., et al., "n–Butyl 2–Cyanoacrylate Substitute for IBCA in Interventional Neuroradiobiology: Histopathologic and Polymerization Time Studies", *AJNR*, 10:777–786 (1989).

Buice, R.G., et al., "The Plasma Time Course of Orally–Administered Cyclosporine in the Dog", *Res Comm in Chem Path Pharm*, 50(1):143–146 (1985).

Casarett and Doull's *Toxicology*, Amdur, M.O., et al., Ed., Pergamon Press, New York, pp. 661–664 (1975).

Castañeda–Zuñiga, et al., *Interventional Radiology*, in Vascular Embolotherapy, Part 1, 1:9–32, Williams & Wilkins, Publishers (1992).

Chaloupka, J.C., et al., "Technical Efficacy and Histopathologic Studies of a New Liquid Embolic Agent: EVAL in the Swine Rete Endovascular Embolization Model", (abstr.), *Am J Roentgenol*, 160(4):115–116 (1993).

Chaloupka, J.C., et al., "An in vivo Arteriovenous Malformation Model in Swine: Preliminary Feasibility and Natural History Study", *AJNR*, 15:945–950 (1994).

Chaloupka, J.C., et al., "Technical feasibilty and histopathologic studies of ethylene vinyl alcohol copolymer (EVAL) in the swine endovascular embolization model", *AJNR*, 15:1107–1105 (1994).

Christensen, J.M., et al., "Ethyl Lactate–Ethanol–Water Cosolvent for Intravenous Theophylline", *Res Comm in Chem Path Pharm*, 50(1):147–150 (1985).

Grosshans, E., et al., "Clinical evaluation of a topical ethyl lactate treatment of acne vulgaris", *Ann Dermatol Venereol*, 105:833–838 (1978) [in French].

Kinugasa, K., et al., "Direct Thrombosis of Aneurysms with Cellulose Acetate Polymer", *J Neurosurg*, 77:501–507 (1992).

Kinugasa, K., et al., "Prophylactic Thrombosis to Prevent New Bleeding and to Delay Aneurysm Surgery", *Neurosurg*, 36(4):661–667 (1995).

Kinugasa, K., et al., "Early Treatment of Subarachnoid Hemorrhage After Preventing Rerupture of an Aneurysm", *J Neurosurg*, 83:34–41 (1995).

Laurent, A., et al., *Abstract No. 299*, for "Injectable Gel–Giving Solutions for Embolization. Hydrodynamic and Animal Studies", Meeting of Interventional Radiology (1996).

Lylyk, P., et al., "Use of new mixture for embolization of intracranial vascular malformations: Preliminary experimental experience", *Neurorad*, 32:304–310 (1990).

Mandai, S., et al., "Direct Thrombosis of Aneurysms with Cellulose Acetate Polymer", *J Neurosurg*, 77:497–500 (1992).

Marot, L., et al., "Allergic contact dermatitis of ethyl lactate", *Contact Dermatitis*, 17:45–46 (1997).

Prottey, C., et al., "The mode of action of ethyl lactate as a treatment for acne", *Br J Dermatol*, 110:475–485 (1984).

Sampei, K., et al., "Histological Changes in Brain Tissue and Vasculature after Intracarotid Infusion of Organic Solvents in Rats", *Interven Neurorad*, 38:291–294 (1996).

Shaw, D.A., et al., "Reduction of Oral Tetracycline of Lipolysis of Triglycerides in Hair Lipid", *Acta Derm Venerol*, 60:83–85 (1980).

Taki, W., et al., "Selection and Combination of Various Endovascular Techniques in the Treatment of Giant Aneurysms", *J Neurosurg*, 77:37–42 (1992).

*Primary Examiner*—John Pak
*Assistant Examiner*—Frank Choi
*Attorney, Agent, or Firm*—Burns, Doane, Swecker & Mathis, LLP

[57] ABSTRACT

Disclosed are novel compositions for embolizing blood vessels which are particularly suited for treating vascular lesions via catheter delivery. In one embodiment, the compositions of this invention comprise a biocompatible polymer, ethyl lactate solvent and a biocompatible contrast agent.

17 Claims, No Drawings

VASCULAR EMBOLIZING COMPOSITIONS COMPRISING ETHYL LACTATE AND METHODS FOR THEIR USE

BACKGROUND OF THE INVENTION

Field of the Invention

This invention is directed to novel compositions for embolizing blood vessels which are particularly suited for treating vascular lesions via catheter delivery of the composition and methods for their use. In particular, the compositions of this invention comprise a biocompatible polymer and ethyl lactate as the embolic solvent. The compositions and methods of this invention overcome art recognized problems of known embolic solvents such as ethanol and dimethylsulfoxide.

References

The following publications are cited in this application as superscript numbers:

1 Mandai, et al., "Direct Thrombosis of Aneurysms with Cellulose Acetate Polymer", J Neurosurg, 77:497–500 (1992)

2 Kinugasa, et al., "Direct Thrombosis of Aneurysms with Cellulose Acetate Polymer", J Neurosurg, 77:501–507 (1992)

3 Casarett and Doull's Toxicology, Amdur, et al., Editors, Pergamon Press, New York, pp. 661–664 (1975)

4 Greff, et al., U.S. Pat. No. 5,667,767 for "Novel Compositions for Use in Embolizing Blood Vessels", issued Sep. 16, 1997

5 Greff, et al., U.S. Pat. No. 5,580,568 for "Cellulose Diacetate Compositions for Use in Embolizing Blood Vessels", issued Dec. 3, 1996

6 Kinugasa, et al., "Early Treatment of Subarachnoid Hemorrhage After Preventing Rerupture of an Aneurysm", J Neurosurg, 83:34–41 (1995)

7 Kinugasa, et al., "Prophylactic Thrombosis to Prevent New Bleeding and to Delay Aneurysm Surgery", Neurosurg, 36:661 (1995)

8 Taki, et al., "Selection and Combination of Various Endovascular Techniques in the Treatment of Giant Aneurysms", J Neurosurg, 77:3742 (1992)

9 Evans, et al., U.S. Pat. No. 5,695,480 for "Novel Compositions for Use in Embolizing Blood Vessels", issued Dec. 9, 1997

10 Castaneda-Zuniga, et al., Interventional Radiology, in Vascular Embolotherapy, Part 1, 1:9–32, Williams & Wilkins, Publishers (1992)

11 Rabinowitz, et al., U.S. Pat. No. 3,527,224, for "Method of Surgically Bonding Tissue Together", issued Sep. 8, 1970

12 Hawkins, et al., U.S. Pat. No. 3,591,676, for "Surgical Adhesive Compositions", issued Jul. 6, 1971

13 Evans, et al., U.S. patent application Ser. No. 08/655,987, for "Methods for the Reversible Sterilization of Male Mammals", filed May 31, 1996 as Attorney Docket No. 018413-007 now abandoned 14 Evans, et al., U.S. patent application Ser. No. 08/656,394, for "Methods for the Reversible Sterilization of Female Mammals", filed May 31, 1996 as Attorney Docket No. 018413-014 now abandoned 15 Sampei, et al., Interventional Neuroradiology, for "Histological Changes in Brain Tissue and Vasculature after Intracarotid Infusion of Organic Solvents in Rats", 38:291 (1996)

16 Laurent, et al., Abstract No. 299, for "Injectable Gel-Giving Solutions for Embolization. Hydrodynamic and Animal Studies", Meeting of Interventional Radiology (1996)

17 Chaloupka, Amer Jour Neur Rad, 15:1107 (1994)

18 Chaloupka, et al., "An in vivo Arteriovenous Malformation Model in Swine: Preliminary Feasibility and Natural History Study", AJNR, 15:945–950 (1994)

19 Brothers, et al., "N-Butyl 2-cyanoacrylate Substitute for IBCA in interventional neuroradiobiology; histopathologic and polymerization time studies", AJNR, 10:777–786 (1989)

20 Lylyk, et al., "Use of a mixture for embolization of intracranial vascular malformations: preliminary experimental experience", Neuroradiology, 32:304–310 (1990)

21 Chaloupka, et al., "Technical feasibility and histopathologic studies of ethylene vinyl alcohol copolymer (EVAL) in the swine endovascular embolization model" (abstr.), Am J Roentgenol, 160:115–116 (1993)

22 Christensen, et al., "Ethyl Lactate-Ethanol-Water Cosolvent for Intravenous Theophylline", Research Communications in Chemical Pathology and Pharmacology, 50:143–150 (1985)

23 Prottey, et al., "The mode of action of ethyl lactate as a treatment for acne", Br J Dermatol, 110:475–85 (1984)

24 Shaw, et al., "Reduction of oral tetracycline of lipolysis of triglycerides in hair lipid", Acta Derm Venerol, 60:83–85 (1980)

25 Grosshans, et al., "Clinical evaluation of a topical ethyl lactate treatment of acne vulgaris", Ann Dermatiol Venereol, 105:833–838 (1978) [in French]

26 Marot, et al., "Allergic contact dermatitis of ethyl lactate", Contact Dennatitus, 17:45–46 (1997)

27 Evans, et al., U.S. Pat. No. 5,695,480 for "Novel Embolizing Compositions", issued on Dec. 9, 1997.

The disclosures of each of the above references are herein incorporated by reference in their entirety to the same extent as if each individual reference was specifically and individually indicated to be incorporated herein by reference in its entirety.

State of the Art

Embolization of blood vessels is conducted for a variety of purposes including the treatment of tumors, the treatment of lesions such as aneurysms, arteriovenous malformations (AVM), arteriovenous fistula (AVF), uncontrolled bleeding and the like.

Embolization of blood vessels is preferably accomplished via catheter techniques which permit the selective placement of the catheter at the vascular site to be embolized. In this regard, recent advancements in catheter technology as well as in angiography now permit neuro endovascular intervention including the treatment of otherwise inoperable lesions. Specifically, development of microcatheters and guide wires capable of providing access to vessels as small as 1 mm in diameter allows for the endovascular treatment of many lesions.

Endovascular treatment regimens preferably include visualization of delivery of the embolizing compositions. This may be accomplished using ultrasound or other non-contrast means. However, the use of a radiopaque contrast agent, in particular a water insoluble contrast agent, in the embolizing compositions allows the physician to visualize delivery of the composition to the vascular site via conventional techniques such as fluoroscopy.[1-8] Visualization, however accomplished, is particularly necessary when using catheter delivery techniques in order to ensure both that the composition is being delivered to the intended vascular site and that the requisite amount of composition is delivered.

When delivered by catheter, the embolic compositions commonly comprise a biocompatible solvent such as ethanol, dimethylsulfoxide (DMSO) or aqueous solutions of ethanol or DMSO and a biocompatible polymer. Preferably, the compositions further comprise a contrast agent. The biocompatible solvent is miscible or soluble in blood or other body fluid and also solubilizes the biocompatible polymer during delivery. The biocompatible polymer is selected to be soluble in the biocompatible solvent but insoluble in blood or other body fluid. The contrast agent, when used, is dissolved or suspended in the composition and, as above, permits the physician to fluoroscopically visualize catheter delivery of this composition. Upon contact with the blood or other body fluid, the biocompatible solvent dissipates from the embolic composition whereupon the biocompatible polymer precipitates and embolizes the blood vessel.

In practice, complications in this procedure have been reported when using catheter delivery of the embolizing composition to the vascular site. For example, Sampei, et al.,[15] Laurent, et al.[16] and Chaloupka[17] report that intra-arterial infusion of embolizing compositions containing even a small volume of DMSO produces local toxicity to the blood vessel.

Specifically, Chaloupka reported vasospasms, hemorrhage and ultimately death in the laboratory animals injected with DMSO and concluded that DMSO was angiotoxic. Sampei, et al.[15] report severe vasospasms arising from intra-arterial infusion of DMSO, which often results in cerebral infarction, and at a larger volume gross, angionecrosis of small cerebral arteries resulting in subarachnoid hemorrhage. Sampei, et al.[15] further report that the intra-arterial infusion of anhydrous DMSO or concentrated ethanol (e.g., 70% ethanol) can produce severe histopathological changes and can possibly accelerate thrombosis of vessels distal to the injection. Based on the above, Sampei, et al.[15] conclude that the embolic composition should contain a low concentration of ethanol.

Notwithstanding the above, the use of an embolic solvent which permits sufficient concentrations of a water insoluble polymer composition to be generated is preferred.

There is little published on the vascular and cardiovascular effects of ethyl lactate infusions. Christensen, et al.[22] report on a study evaluating the degree of hemolysis of erythrocytes that occurs when a cosolvent system of ethyl lactate-ethanol-water is incubated with red blood cells and the effects of the cosolvent system on the pharmacokinetics of theophylline in rabbits. The pure cosolvent had a mild hemolytic activity, with no indication that any of the rabbits experienced any discomfort during the administration of theophylline dissolved in the cosolvent system. Respiratory and pulse rates were monitored regularly in the rabbits throughout the study and did not change. The majority of the medical literature on ethyl lactate is in its use as part of a topical treatment for acne.[22-25] There are no adverse effects reported except for a brief report of one patient experiencing allergic contact dermatitis.[26]

In view of the above, there is an ongoing need for a fully biocompatible embolic solvent which allows sufficient polymer solubility in the embolic composition without producing undesirable side effects.

SUMMARY OF THE INVENTION

This invention is directed in part to the novel and unexpected discovery that the use of ethyl lactate as the embolic solvent allows for sufficient solubility of biocompatible polymer in the embolizing composition while producing a composition which is fully biocompatible and without undesirable toxic side effects. Because lactate occurs naturally in the body, it is non-toxic when infused in a vessel.

Accordingly, in one of its composition aspects, this invention is directed to a composition comprising a biocompatible polymer and ethyl lactate, wherein the polymer has a solubility of at least 0.04 g/mL at 20° C. in ethyl lactate. Compositions comprising cellulose acetates and, particularly, cellulose diacetate as the polymer are preferred, as are compositions comprising a contrast agent, more particularly an insoluble contrast agent, and, most particularly a contrast agent with an average particle size of 1 to 10 $\mu$m.

In one of its method aspects, this invention is directed to a method for embolizing a blood vessel by delivering via a catheter into said blood vessel a composition comprising a biocompatible polymer and ethyl lactate, wherein the polymer has a solubility of at least 0.04 g/mL at 20° C. in ethyl lactate under conditions where a precipitate is formed, which precipitate embolizes the blood vessel.

In one of its kit aspects, this invention is directed to a kit of parts comprising a polymer composition comprising a biocompatible polymer and ethyl lactate, wherein the polymer has a solubility of at least 0.04 g/mL at 20° C. in ethyl lactate and a catheter. In a preferred embodiment, the kit further comprises a microballoon catheter to attenuate or arrest blood flow.

DETAILED DESCRIPTION OF THE INVENTION

This invention is directed to novel compositions comprising ethyl lactate for embolizing blood vessels which are particularly suited for treating vascular lesions via catheter delivery of the composition.

Prior to discussing this invention in further detail, the following terms will first be defined:

The term "embolizing" refers to a process wherein a material is injected into a blood vessel which, in the case of, for example, aneurysms, fills or plugs the aneurysm sac and/or encourages clot formation so that blood flow into the aneurysm ceases, and in the case of AVM's and AVF's forms a plug or obstruction to control/reroute blood flow to permit proper tissue perfusion. Embolization of the blood vessel is, therefore, important in preventing/controlling bleeding due to lesions (e.g., organ bleeding, gastrointestinal bleeding, vascular bleeding as well as bleeding associated with an aneurysm). In addition, embolization can be used to ablate diseased tissue (e.g., tumors, etc.) by cutting off its blood supply.

The term "biocompatible polymer" refers to polymers which, in the amounts employed, are non-toxic, chemically inert, and substantially non-immunogenic when used internally in the patient and which are substantially insoluble in blood. Suitable biocompatible polymers include, by way of example, cellulose acetates[2,6-7] (including cellulose diacetate[5]), cellulose acetate copolymers (including cellulose acetate butyrate), ethylene vinyl alcohol copolymers,[4,8] hydrogels (e.g., acrylics), polyacrylonitrile, polyvinylacetate, nitrocellulose, copolymers of urethane/carbonate, copolymers of styrene/maleic acid, and mixtures thereof.[9] Preferably, the biocompatible polymer is also non-inflammatory when employed in situ.

The particular biocompatible polymer employed is not critical so long as it has a solubility in ethyl lactate of at least 0.04 g/mL at 20° C. and is selected relative to the viscosity of the resulting polymer solution, and the like. Such factors are well within the skill of the art.

Preferred biocompatible polymers include cellulose acetates and, particularly, cellulose diacetate. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. Preferably, the cellulose diacetate is selected such that a solution of 8 weight percent in ethyl lactate has a viscosity of 80–100 centipoise at 20° C. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

The term "contrast agent" refers to a biocompatible (non-toxic) radiopaque material capable of being monitored during injection into a mammalian subject by, for example, radiography or fluoroscopy. The contrast agent can be either water soluble or water insoluble. Examples of water soluble contrast agents include metrizamide, iopamidol, iothalamate sodium, iodomide sodium, and meglumine.

The term "water insoluble contrast agent" refers to a water insoluble (i.e., has a water solubility of less than 0.01 mg/mL at 20° C.), radiopaque material capable of being monitored during injection into a mammalian subject by, for example, radiography. Examples of water insoluble contrast agents include tantalum, tantalum oxide, tungsten, and barium sulfate, which are commercially available in the proper form for in vivo use. Methods for preparing such water insoluble biocompatible contrast agents having an average particle size of about 10 μm or less have been described. Other water insoluble contrast agents include gold and platinum.

The term "ethyl lactate" refers to the biocompatible embolic solvent of the present invention of the formula $CH_3CHOHCOOC_2H_5$ which is an organic material liquid at least at room temperature with a boiling point of 154° C. in which biocompatible polymers are soluble. It is miscible in water and, in the amounts used, is substantially non-toxic. Analogues, homologues and isomers of ethyl lactate are also included in this term. Aqueous mixtures with the ethyl lactate can be employed provided that the amount of water employed is sufficiently small that the dissolved polymer precipitates upon contact with the blood. Likewise small amounts of compatible solvents (e.g., <20%) can be used. Such compatible solvents include DMSO, ethanol, etc.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

Compositions

The polymer compositions employed in the methods of this invention are prepared by conventional methods whereby each of the components is added and the resulting composition mixed together until the overall composition is substantially homogeneous.

The biocompatible embolic solvent used in the present invention is ethyl lactate. Ethyl lactate is degraded into lactic acid and ethanol. These degradation products occur naturally in the body, making ethyl lactate fully biocompatible. This is in contrast with DMSO which is a foreign substance which must be detoxified by the liver to eliminate it from the body.

For example, polymer compositions can be prepared by adding sufficient amounts of the biocompatible polymer to the ethyl lactate solvent to achieve the effective concentration for the polymer composition. Preferably, the polymer composition will comprise from about 2.5 to about 8.0 weight percent of the biocompatible polymer composition based on the total weight of the polymer composition and more preferably from about 4 to about 7.0 weight percent. If necessary, gentle heating and stirring can be used to effect dissolution of the biocompatible polymer into the biocompatible ethyl lactate solvent, e.g., 12 hours at 50° C.

When a contrast agent is used, sufficient amounts of the contrast agent are then added to the ethyl lactate solvent to achieve the effective concentration for the complete composition. Preferably, the composition will comprise from about 10 to about 40 weight percent of the contrast agent and more preferably from about 20 to about 40 weight percent and even more preferably about 30 weight percent. Insofar as the contrast agent may not be soluble in the ethyl lactate, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

The particular order of addition of components to the ethyl lactate is not critical and stirring of the resulting suspension is conducted as necessary to achieve homogeneity of the composition. Preferably, mixing/stirring of the composition is conducted under an anhydrous atmosphere at ambient pressure. The resulting composition is preferably heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, γ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the ethyl lactate, the polymers described herein are preferably not cross-linked.

Methods

The compositions described above can then be employed in methods for the catheter assisted embolization of mammalian blood vessels. In such methods, a sufficient amount of this composition is introduced into the selected blood vessel via a catheter delivery means under fluoroscopy so that upon precipitation of the polymer, the blood vessel is embolized. The particular amount of embolizing composition employed is dictated by the total volume of the vasculature to be embolized, the concentration of polymer in the composition, the rate of precipitation (solids formation) of the polymer, etc. Such factors are well within the skill of the art.

One particularly preferred method for catheter delivery of the embolizing compositions of this invention to the selected vascular site is via a small diameter medical catheter. The particular catheter employed is not critical provided that polymeric catheter components are compatible with the embolizing composition (i.e., the catheter components will not readily degrade in the embolizing composition). In this regard, it is preferred to use materials in the catheter components which are inert in the presence of the embolizing composition described herein. Such materials compatible with the embolizing compositions can be readily determined by the skilled artisan and include, for example, polyethylene, other polyolefins, fluoropolymers (e.g., Teflon™), silicone, etc.

One particularly preferred method for the catheter injection of the compositions of this invention is as follows:

1. Microcatheter placement in vivo is confirmed by injection of water soluble contrast agent;
2. The cap on the 3 French (O. D.) microcatheter luer hub is secured and, if used, the contrast agent in the composition is fully dispersed by vigorous shaking and then setting this aside;
3. Aspirate 0.8 cc of sterile ethyl lactate into a 1 cc syringe. Remove cap from microcatheter hub. Inject 0.30 cc of ethyl lactate for a typical 150 cm microcatheter. Remove the syringe and overfill/wash the luer hub with another 0.3 cc of ethyl lactate. Immediately place and secure the cap on the microcatheter luer hub to prevent backflow and mixing;
4. Again, shake the composition well to fully disperse the contrast agent. Fill a 1 cc syringe with the composition through a 21 gauge needle. Remove cap from microcatheter hub, fill any air space in the hub with the remaining ethyl lactate and immediately connect the composition syringe to the catheter hub, making sure that there is no air in the hub during the connection;
5. With the composition syringe pointing up to create a sharp interfacial boundary between the ethyl lactate and the embolic composition, slowly inject the first 0.25 cc to displace the ethyl lactate in the microcatheter and dilute the ethyl lactate in the blood;
6. Under fluoroscopy, the embolic composition should be visible in the distal portion of the microcatheter body. Lower the syringe tip and inject the embolic composition as the clinical situation requires. Monitor the volume of the embolic composition injected to correspond to the volume of the vascular space being filled; and
7. Upon completion of the embolic composition injection, gently aspirate with the embolic syringe to separate the catheter tip from the embolic composition mass. Wait a few seconds, release the syringe plunger and withdraw the microcatheter.

In this protocol, the dead space for the 150 cm microcatheter is about 0.32 cc.

In the case of aneurysms, the mammal is preferably rotated to place the aneurysm in a downward position to encourage displacement of aneurysmal blood.

When introduced into the vascular site, the ethyl lactate solvent diffuses into the blood and a solid precipitate forms which precipitate is the water insoluble polymer, optionally with the contrast agent encapsulated therein. Without being limited to any theory, it is believed that initially, a soft gel to spongy solid precipitate forms upon contact with the blood. This precipitate then restricts blood flow, entrapping red cells thereby causing clot embolization of the blood vessel.

Utility

The compositions described herein are useful in embolizing mammalian blood vessels which, in turn, can be used to prevent/control bleeding (e.g., organ bleeding, gastrointestinal bleeding, vascular bleeding, bleeding associated with an aneurysm) or to ablate diseased tissue (e.g., tumors, etc.). Accordingly, these compositions find use in human and other mammalian subjects requiring embolization of blood vessels. Additionally, these compositions can be used in the reversible sterilization of mammalian patients as described in the applications by Evans, et al.,[13,14] as urologic bulking agents or in plastic and reconstructive surgery.

It is contemplated that these compositions can be employed as a carrier for a compatible pharmaceutically active compound wherein this compound is delivered in vivo for subsequent release. Such compounds include, by way of example only, antibiotics, promoters and inhibitors of angiogenesis, anti-inflammatory agents, cytotoxic and chemotherapeutic agents, and the like.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

cc=cubic centimeter
cm=centimeter
DMSO=dimethylsulfoxide
EVOH=ethylene vinyl alcohol copolymer
g=gram
ID=internal diameter
in.=inch
min.=minute
mL=milliliter
mm=millimeter
OD=outer diameter
sec.=seconds
µm=micron Example 1

Preparation of an Ethyl Lactate Cellulosic Solution

Cellulose diacetate (39.8% acetyl) was dissolved in ethyl lactate at a concentration of 8% weight per volume, resulting in a clear solution having a viscosity of about 80–100 centipoise. Injection of 0.1 to 0.3 mL of this ethyl lactate cellulosic solution into saline resulted in the immediate formation of a coherent, white spongy mass. Solvent diffusion from the precipitating mass was slower than with DMSO.

Example 2

Preparation of Ethyl Lactate Polymer Compositions With Tantalum Contrast Agent

A composition comprising 7% (w/v) of cellulose diacetate in ethyl lactate with 30% (w/v) tantalum powder was prepared using a HEPA clean hood and proper gowning attire (hairnet, gloves, gown and shoe covers).

A stock solution (15 cc) with tantalum added was prepared in a 20 cc screw cap bottle with Teflon cap liner as follows: 1.05 g of cellulose diacetate was added to 15.0 mL of ethyl lactate (Aldrich E3410-2), using a pipet for transfer. The bottle was briefly flushed with filtered, dry, prepurified nitrogen and capped. Exposure of ethyl lactate to air was minimized, as ethyl lactate is hydroscopic and degrades in the presence of moisture into ethyl alcohol and lactic acid. The composition was shaken gently and often to dissolve. Heat was not used to aid dissolution. Then, 4.5 g of tantalum micronized powder was added to the bottle, which was flushed with nitrogen, capped and shaken gently for 1.0 minute. This gave a composition of 7% (w/v) cellulose diacetate and 30% (w/v) tantalum in ethyl lactate. Then, 2.5 cc aliquots were transferred into six 3.0 cc vials, flushed with nitrogen, capped and half of them sterilized at 125° C. for 60 minutes. Also, six empty vials were filled with the solvent ethyl lactate, flushed with nitrogen, capped, and half of them sterilized at 125° C. for 60 minutes.

A composition comprising 4% (w/v) of a cellulose acetate (in this case, cellulose diacetate) in ethyl lactate with 30% (w/v) tantalum powder was prepared as described above. The viscosity of the cellulose acetate ethyl lactate solution at 25° C. prior to addition of tantalum was nominally 31 centiStokes (cSt).

Example 3

Embolization of Blood Vessels

The purpose of this example is to illustrate a specific protocol for embolizing mammalian blood vessels using the compositions of this invention. This example employed a swine with rete mirabile (a well accepted AVM model[18-21]) located in the lower portions (left and right) of the skull base.

The swine was anesthetized. A sterilized composition of 4% (w/v) cellulose acetate in ethyl lactate with 30% (w/v) tantalum, prepared as in Example 2 above, was used.

The right rete was accessed via a 150 cm polyolefin microcatheter, 0.3 cc of ethyl lactate injected into the microcatheter, then a syringe containing the 4% (w/v) composition from Example 2 was attached to the catheter. The ethyl lactate in the catheter was cleared in 65 seconds, followed by the 4% (w/v) cellulose acetate ethyl lactate composition. The ethyl lactate composition material flowed easily and the entire rete was embolized. Approximately 0.5 mL of the cellulose acetate ethyl lactate composition was administered. The degree of penetration and ability to control the flow of the material were very good for this composition.

After post embolization angiograms, the animal was sacrificed. The rete and the brain were harvested for histopathological study, and stored in formalin. On visual examination of the rete, the right rete was found to be 100% embolized. The coronal retial plexis was filled, and large portions of the internal carotid, MCA, and PCA were also embolized with the cellulose acetate. The left rete appeared normal. No attempt was made to limit the cellulose acetate to the right rete.

From the foregoing description, various modifications and changes in the composition and method will occur to those skilled in the art. All such modifications coming within the scope of the appended claims are intended to be included therein.

What is claimed is:

1. A composition suitable for use in therapeutically embolizing blood vessels which composition comprises:

(a) a solution of a biocompatible chemically inert polymer and ethyl lactate; and (b) a contrast agent selected from the group consisting of a water insoluble contrast agent and a water soluble contrast agent, wherein the polymer has a solubility of at least 0.04 g/mL at 20° C. in ethyl lactate.

2. The composition according to claim 1 wherein said contrast agent is a water insoluble contrast agent selected from the group consisting of tantalum, tantalum oxide, tungsten, and barium sulfate.

3. The composition according to claim 2 wherein said contrast agent has an average particle size of from 1 to 10 microns.

4. The composition according to claim 2 wherein said contrast agent is tantalum.

5. The composition according to claim 1 wherein said biocompatible polymer is a cellulose acetate.

6. The composition according to claim 5 wherein said biocompatible polymer is cellulose diacetate.

7. A method for therapeutically embolizing a blood vessel by delivering via a catheter into said blood vessel a composition comprising:

(a) a solution of a biocompatible, chemically inert polymer and ethyl lactate; and (b) a contrast agent selected form the group consisting of a water insoluble contrast agent and a water soluble contrast agent under conditions wherein a precipitate is formed which embolizes the blood vessel, wherein the polymer has a solubility of at least 0.04 g/mL at 20° C. in ethyl lactate.

8. The method according to claim 7 wherein said contrast agent is a water insoluble contrast agent selected from the group consisting of tantalum, tantalum oxide, tungsten, and banium sulfate.

9. The method according to claim 8 wherein said contrast agent has an average particle size of from 1 to 10 microns.

10. The method according to claim 7 wherein said biocompatible polymer is a cellulose acetate.

11. The method according to claim 10 wherein said biocompatible polymer is cellulose diacetate.

12. A lit of parts suitable for use in therapeutically embolizing blood vessels comprising:

Part (a) a polymer composition comprising a solution of a biocompatible, chemically inert polymer and ethyl lactate, and a contrast agent selected from the group consisting of water insoluble contrast agent and a water soluble contrast agent wherein the polymer has a solubility of at least 0.04 g/mL at 20° C. in ethyl lactate; and Part (b) a catheter.

13. The kit of parts according to claim 12 wherein said contrast agent is a water insoluble contrast agent selected from the group consisting of tantalum, tantalum oxide, tungsten, and barium sulfate.

14. The kit of parts according to claim 13 wherein said contrast agent is tantalum.

15. The kit of parts according to claim 12 wherein said biocompatible polymer is a cellulose acetate.

16. The kit of parts according to claim 15 wherein said biocompatible polymer is cellulose diacetate.

17. The kit of parts according to claim 12 which further comprises a microballoon catheter to attenuate or arrest blood flow.

* * * * *